United States Patent
Kovach

(10) Patent No.: US 10,076,328 B2
(45) Date of Patent: Sep. 18, 2018

(54) CLIP DELIVERY SYSTEM FOR HEART VALVE REPAIR AND METHOD OF USE

(71) Applicant: St. Jude Medical, LLC, Abbott Park, IL (US)

(72) Inventor: Melinda K. Kovach, Plymouth, MN (US)

(73) Assignee: St. Jude Medical, LLC, Abbott Park, IL (US)

( * ) Notice: Subject to any disclaimer, the term of this patent is extended or adjusted under 35 U.S.C. 154(b) by 820 days.

(21) Appl. No.: 14/376,321

(22) PCT Filed: Jan. 25, 2013

(86) PCT No.: PCT/US2013/023081
§ 371 (c)(1),
(2) Date: Aug. 1, 2014

(87) PCT Pub. No.: WO2013/116093
PCT Pub. Date: Aug. 8, 2013

(65) Prior Publication Data
US 2015/0057682 A1 Feb. 26, 2015

Related U.S. Application Data

(60) Provisional application No. 61/593,427, filed on Feb. 1, 2012.

(51) Int. Cl.
*A61B 17/10* (2006.01)
*A61F 2/24* (2006.01)
(Continued)

(52) U.S. Cl.
CPC ............ *A61B 17/105* (2013.01); *A61B 17/08* (2013.01); *A61B 17/10* (2013.01); *A61F 2/2442* (2013.01);
(Continued)

(58) Field of Classification Search
CPC .... A61F 2/2442; A61F 2/2445; A61F 2/2451; A61F 2/2454; A61F 2/2457;
(Continued)

(56) References Cited

U.S. PATENT DOCUMENTS 4,548,201 A 10/1985 Yoon
8,062,308 B2 * 11/2011 Noda ............... A61B 17/12013
128/831

(Continued)

FOREIGN PATENT DOCUMENTS

WO 2005032421 A2 4/2005

OTHER PUBLICATIONS

International Search Report and Written Opinion for Application No. PCT/US2013/023081 dated May 3, 2013.
(Continued)

*Primary Examiner* — Ashley Fishback
(74) *Attorney, Agent, or Firm* — Lerner, David, Littenberg, Krumholz & Mentlik, LLP

(57) ABSTRACT

A device for repair of a heart valve leaflet includes an elongated body having a lumen extending therethrough in a longitudinal direction, a proximal end, and an open distal end. The device further includes a plurality of clips disposed at spaced positions within the lumen, the plurality of clips being configured and arranged to couple to a portion of the heart valve leaflet. At least one clip in the plurality of clips and the heart valve leaflet are capable of translation relative to one another in the longitudinal direction.

10 Claims, 8 Drawing Sheets

(51) Int. Cl.
  *A61B 17/08* (2006.01)
  *A61B 17/00* (2006.01)
(52) U.S. Cl.
  CPC ............... *A61B 2017/00243* (2013.01); *A61B 2017/00349* (2013.01); *A61B 2017/00783* (2013.01); *A61F 2250/0071* (2013.01)
(58) Field of Classification Search
  CPC ...... A61F 2/2478; A61F 2/2466; A61B 17/10; A61B 17/105; A61B 17/08; A61B 17/083
  See application file for complete search history.

(56) References Cited

U.S. PATENT DOCUMENTS

| | | |
|---|---|---|
| 2002/0072757 A1 | 6/2002 | Ahmed et al. |
| 2004/0236419 A1 | 11/2004 | Milo |
| 2006/0167474 A1* | 7/2006 | Bloom ................. A61F 2/2466 606/142 |
| 2007/0080188 A1 | 4/2007 | Spence et al. |
| 2007/0225762 A1 | 9/2007 | LaBombard |
| 2007/0250103 A1 | 10/2007 | Makower et al. |
| 2007/0299422 A1* | 12/2007 | Inganas .............. A61B 17/0057 604/508 |
| 2009/0105728 A1 | 4/2009 | Noda et al. |
| 2010/0324669 A1 | 12/2010 | Hlavka et al. |
| 2011/0054521 A1* | 3/2011 | Ventura .............. A61B 17/0057 606/216 |
| 2012/0245603 A1* | 9/2012 | Voss .................. A61B 17/0057 606/151 |

OTHER PUBLICATIONS

Extended European Search Report for EP 16181354.8, dated Nov. 10, 2016, 8 pages.

* cited by examiner

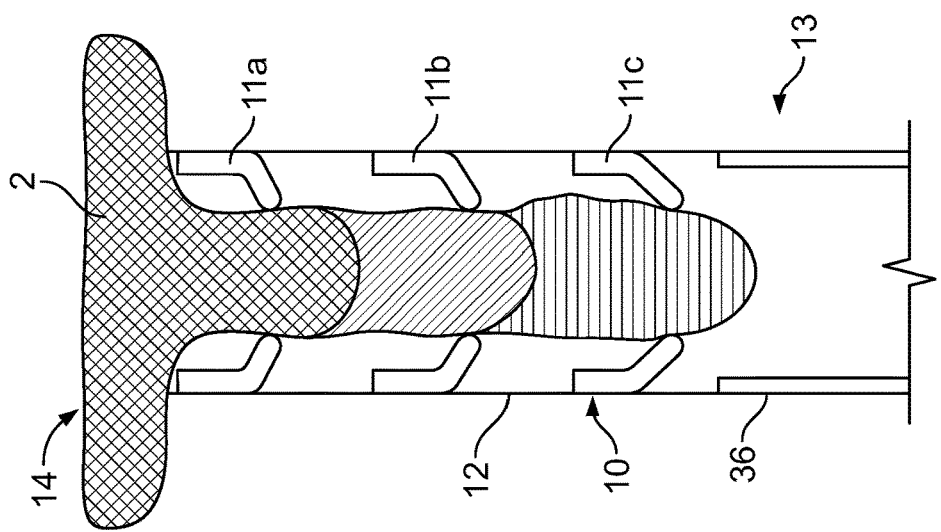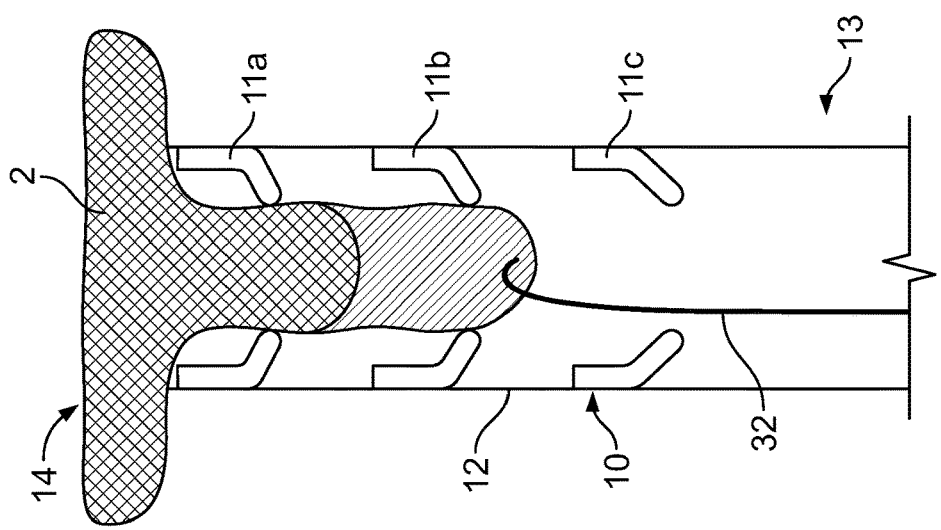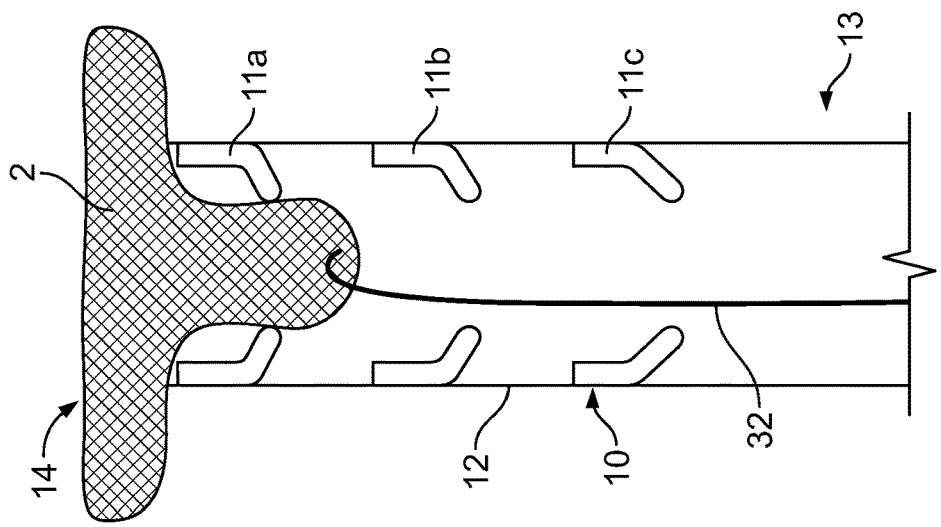

CLIP DELIVERY SYSTEM FOR HEART VALVE REPAIR AND METHOD OF USE

CROSS-REFERENCE TO RELATED APPLICATIONS

The present application is a national phase entry under 35 U.S.C. § 371 of International Application No. PCT/US2013/023081, filed on Jan. 25, 2013, published in English, which claims priority from U.S. Patent Application No. 61/593,427, filed Feb. 1, 2012, all of which are hereby incorporated herein by reference.

BACKGROUND OF THE INVENTION

The present invention is related to tissue repair, and more particularly to devices, systems, and methods for repair of a heart valve leaflet.

Properly functioning heart valves can maintain unidirectional blood flow in the circulatory system by opening and closing, depending on the difference in pressure from one side of the valve to the other. The two atrioventricular valves (mitral and tricuspid valves) are multicuspid valves that prevent backflow from the ventricles into the atria during systole. They are anchored to the wall of the ventricle by chordae tendineae, which prevent the valve from inverting.

The mitral valve is located at the gate of the left ventricle and is made up of two leaflets and a diaphanous incomplete ring around the valve, known as the mitral valve annulus. When the valve opens, blood flows into the left ventricle. After the left ventricle fills with blood and contracts, the two leaflets of the mitral valve are pushed upwards and close, preventing blood from flowing back into the left atrium and the lungs.

Mitral valve prolapse is a type of myxomatous valve disease in which the abnormal mitral valve leaflets prolapse (i.e., a portion of the affected leaflet may be billowed, loose, and floppy). Furthermore, the chordae tendineae may stretch and thus become too long, or the chordae tendineae may be ruptured. As a result, the valve does not close normally and the unsupported valve leaflet may bulge back, or "prolapse," into the left atrium like a parachute. Thus, as the ventricle contracts, the abnormal leaflet may be propelled backwards, beyond its normal closure line and into the left atrium, thereby allowing blood to return to the left atrium and the lungs.

Mitral valve prolapse causes mitral regurgitation. Isolated posterior leaflet prolapse of the human heart mitral valve, i.e., prolapse of a single leaflet, is the most common cause of mitral regurgitation. The exact cause of the prolapse is not clear. Untreated mitral regurgitation may lead to congestive heart failure and pulmonary hypertension.

Despite the various improvements that have been made to devices and methods for mitral valve leaflet repair, there remain some shortcomings. For example, conventional methods of treating mitral valve prolapse include replacement of the mitral valve, clipping the two mitral valve leaflets to one another, and resection of the prolapsed segment using open heart surgery. Such surgical methods are or may be invasive to the patient and may require an extended recovery period. Moreover, traditional approaches may not adequately secure enough tissue to reduce regurgitation to a satisfactory level.

There therefore is a need for further improvements to the current techniques for treating heart valve leaflet prolapse. Among other advantages, the present invention may address one or more of these needs.

BRIEF SUMMARY OF THE INVENTION

One aspect of the disclosure provides a device for repair of a heart valve leaflet including an elongated body having a lumen extending therethrough in a longitudinal direction, a proximal end, and an open distal end. A plurality of clips are disposed at spaced positions within the lumen, the plurality of clips being configured and arranged to couple to a portion of the heart valve leaflet. At least one clip in the plurality of clips and the heart valve leaflet is capable of translation relative to one another in the longitudinal direction.

In one example, the plurality of clips are configured so that the portion of the heart valve leaflet is able to move in one direction relative to the clips but is inhibited from moving in a second direction opposite the one direction. In another example, the plurality of clips includes three clips. In another example, the device further includes a frangible weld to couple the plurality of clips to the elongated body. The plurality of clips may be affixed to the elongated body at the spaced positions. The device may further include a wire slidably disposed within the lumen and configured and arranged to pull the portion of the heart valve leaflet into the lumen through the open distal end. In one example, the wire is slidably disposed in the lumen for movement between a retracted position and a deployed position, the wire being formed of a memory metal, a distal portion of the wire having a linear configuration when the wire is in the retracted position and a hook-shape configuration when the wire is in the deployed position.

In some examples, the device further includes a feeder mechanism interposed between the plurality of clips and the proximal end of the elongated body, and actuating device for actuating the feeder mechanism to move at least one of the plurality of clips toward the open distal end of the elongated body. Each of the plurality of clips may be independently moveable toward the open distal end of the elongated body.

In another aspect of the invention, a device for repair of a heart valve leaflet includes an elongated body having a lumen extending therethrough in a longitudinal direction, a proximal end, and an open distal end. The device also includes a deployment tube disposed with the elongated body, and a plurality of clips coupled to the deployment tube, the plurality of clips being moveable from the deployment tube to the lumen, and being configured and arranged to couple to a portion of the heart valve leaflet within the lumen.

In one example, the deployment tube includes a window for moving ones of the plurality of clips from the deployment tube to the lumen. The device may further include a feeder mechanism interposed between the plurality of clips and the proximal end of the elongated body, the feeder mechanism being operable to sequentially advance the plurality of clips from within the deployment tube to an engagement position within the lumen. The plurality of clips may be disposed within the deployment tube in a compressed condition. The plurality of clips may be held about the deployment tube in an expanded condition.

In another aspect, the invention contemplates a method of repairing a heart valve leaflet including the steps of i) positioning a repair device adjacent the heart valve leaflet of a patient, the repair device including an elongated body having a lumen extending therethrough in a longitudinal direction, a proximal end, and an open distal end, and a plurality of clips disposed at spaced positions within the lumen; ii) drawing a portion of the heart valve leaflet into the lumen through the open distal end of the elongated body to form a gathered leaflet portion; iii) coupling at least one clip in the plurality of clips to the gathered leaflet portion; and iv) releasing the heart valve leaflet from the elongated body while maintaining the at least one clip secured to the gathered leaflet portion.

In one example, the coupling step includes coupling one clip in the plurality of clips to the gathered leaflet portion each time the heart valve leaflet travels a predetermined distance within the lumen. The plurality of clips may be capable of translating in the longitudinal direction within the lumen and the coupling step may include: (i) coupling one clip in the plurality of clips to the gathered leaflet portion at a first position; (ii) translating the gathered leaflet portion with the coupled clip in the longitudinal direction from a first position to a more proximal position within the lumen; and (iii) successively repeating steps (i) and (ii) until a desired number of clips have been coupled to the gathered leaflet portion.

In one example, the predetermined distance is about 1 mm. In another example, the drawing step includes pulling the heart valve leaflet with a wire slidably disposed within the lumen. At least one of the elongated body or a clip in the plurality of clips may be formed from an echogenic material. In another example, the method further includes moving at least one of the plurality of clips toward the open distal end of the elongated body prior to the coupling step. The releasing step includes detaching the at least one clip from the elongated body and removing the elongated body from the patient.

BRIEF DESCRIPTION OF THE DRAWINGS

Various embodiments of the present invention will now be discussed with reference to the appended drawings. It should be appreciated that these drawings depict only some embodiments of the invention and are therefore not to be considered limiting of its scope.

FIGS. 3A-3C are highly schematic longitudinal cross-sections of the device of FIG. 2A showing various valve leaflet positions during a repair procedure in accordance with the present invention;

DETAILED DESCRIPTION

As used herein, the terms "proximal" and "distal" are to be taken as relative to a user (e.g., a surgeon or an interventional cardiologist) using the disclosed devices. "Proximal" is to be understood as relatively close to the user and "distal" is to be understood as relatively farther away from the user. The invention will be described in connection with the repair of a mitral valve leaflet, but it may also be useful in the repair of other types of cardiac valves or in the gathering and securing of other types of loose body tissue.

Figure 1:
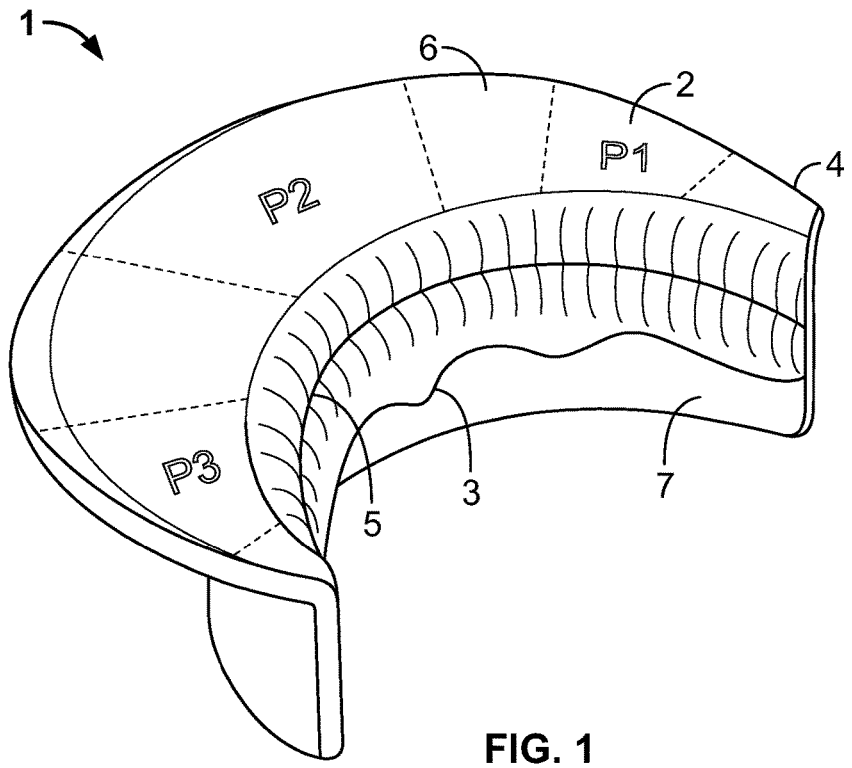
FIG. 1 is a diagrammatic perspective view of a posterior leaflet of a mitral valve.

As shown in FIG. 1, an exemplary mitral valve 1 includes a posterior leaflet 2 and a portion of an anterior leaflet 3. The leaflets 2 and 3 extend from an annulus 4 to a coaptation line 5 where the leaflets meet. The posterior leaflet 2 has an upper portion 6 that is generally perpendicular to the direction of blood flow through the valve 1 and extends between the annulus 4 and the coaption line 5. Additionally, the posterior leaflet 2 has a lower portion 7 that is generally parallel to the direction of blood flow through the valve 1 and extends below the coaption line 5. The posterior leaflet 2 has three scalloped portions P1, P2, and P3, any of which may include a portion that is billowed, loose, or floppy, and therefore be the cause of a prolapse condition of the valve. The inventive devices, systems, and methods described herein may be adapted to repair such a billowed, loose, or floppy portion of the posterior leaflet 2 or the anterior leaflet 3.

Figure 2A:
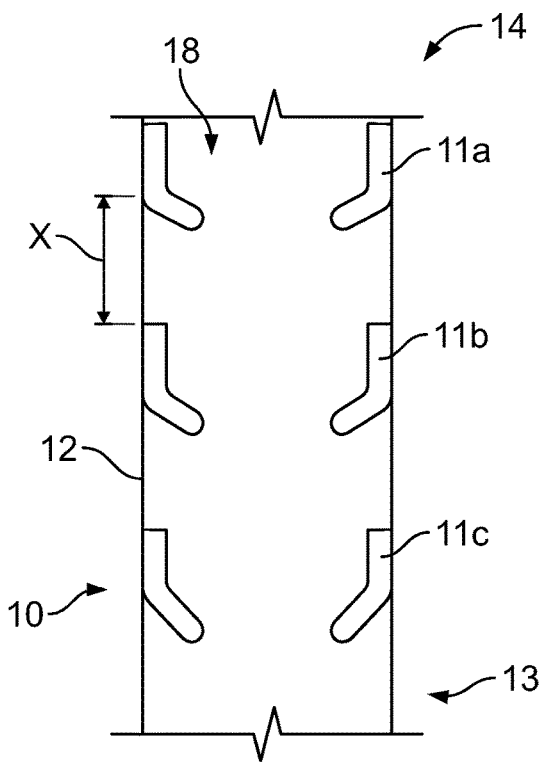
FIG. 2A is a highly schematic longitudinal cross-section of one embodiment of a device for repairing heart valve leaflets in accordance with the present invention.

Referring to FIG. 2A, an exemplary device 10 for repair of heart valve leaflet tissue may include an elongated body or catheter assembly 12 adapted to be inserted into the left atrium or left ventricle of a human heart so that a distal end portion 14 of the catheter assembly may reach the patient's mitral valve for repair thereof. The device 10 may be employed near the posterior leaflet 2, the anterior leaflet 3 or any other suitable tissue within the heart or similar tissue.

The body 12 includes a proximal end 13 and a distal end 14. The body 12 serves as a delivery device and may be formed of any hollow tube, shaft or sheath having a longitudinal lumen 18. The lumen 18 may be formed through the axial center of the body 12. As seen in FIG. 2A, the lumen 18 defines an opening at the distal end 14 of the body 12. It will be understood that the shape and size of the opening may be modified as necessary.

Disposed within the lumen 18 are a number of clips 11. As used herein, the term "clip" refers to any clip, clasp, staple or other suitable fastener capable of holding body tissue in a gathered configuration. The clips 11 may be formed of a shape memory metal such as, for example, nitinol. While FIG. 2A illustrates a configuration having three clips 11a, 11b and 11c, it will be understood that any number of clips 11 may be employed as necessary. Thus, the present invention contemplates devices having one, two, three, four, five or more clips 11.

Figure 2D:
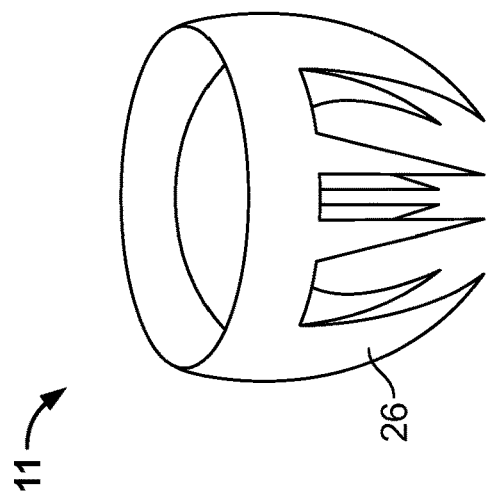
FIGS. 2B-D are a perspective view of several embodiments of clips for use in the present invention.
Figure 2C:
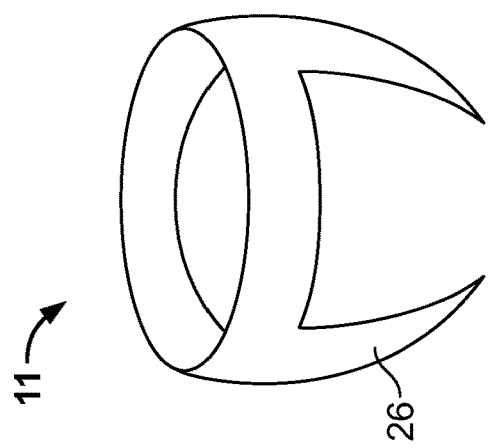
Figure 2B:
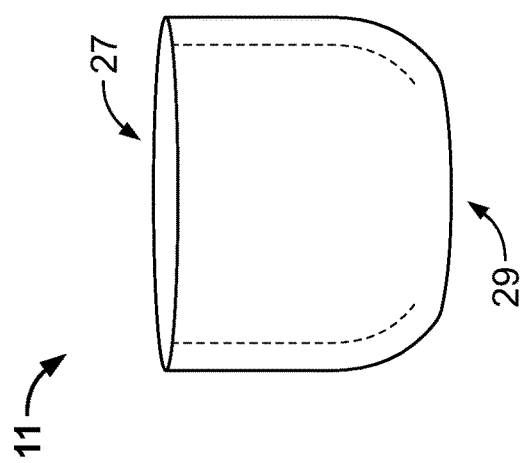

As seen in FIG. 2B, clip 11 may generally have a bowl shape with an opening 27 at one end that is larger in diameter and cross-section than the opening 29 at the other end. As the leaflet 2 is pulled through the clip 11, it is squeezed and compressed from its entrance at opening 27 to its exit at opening 29, expanding slightly as it exits the clip. The clip 11 thereby becomes affixed to the leaflet 2. It will be understood that various configurations of the clips 11 may be used to secure the gathered leaflet 2. The clips 11 may change shape as they are applied to the leaflet 2, flexing slightly at either opening 27 or opening 29 in a sort of ratcheting action. This ratcheting action may be enhanced by providing clip 11 with a plurality of slits (not shown) extending from opening 29 partially along the length of the clip toward opening 27. These slits would divide the body of the clip at opening 29 into a plurality of segments capable of deflecting outwardly independently of one another, but biased to return to the original shape of the clip. As leaflet 2 is pulled through the clip 11, some of these segments may deflect outwardly by a greater amount than others, depending on the shape of the gathered leaflet and the force it exerts on the clip. However, once the relative movement between clip 11 and the leaflet 2 has stopped, the segments will attempt to return to the original shape of the clip, thereby securely engaging the leaflet. Hence, the provision of these slits may make it easier to pull the leaflet tissue through clip 11 without interfering with the ability of the clip to become securely affixed to the leaflet. In still other arrangements, the clips 11 may have a different shape which still enables the leaflet 2 to he pulled through the clip to affix the clip to the leaflet.

Rather than a bowl shape as seen in FIG. 2B, clip 11 may include an annular region at the top and multiple teeth to capture tissue. FIG. 2C illustrates one such clip 11, having two teeth 26. Teeth 26 may function as a ratchet as described above. Additionally, clip 11 may include any number of teeth 26. For example, FIG. 2D illustrates a clip 11 having eight teeth. It will be understood that a clip 11 may include one, two, three, four, six, eight or any other number of teeth 26.

Returning to FIG. 2A, the plurality of clips 11 may be arranged in series in the longitudinal direction of lumen 18, with the clips oriented so the larger opening 27 faces toward the open distal end 14 of body 12. A longitudinal distance x may separate each of the clips 11 from the nearest adjacent clip. This distance x between clips 11 may be from about 0 mm (i.e., the clips contact one another) to about 10 mm, and may be adjusted as necessary. Preferably, the clips 11 are separated from one another by about 1 mm to about 5 mm. Furthermore, each clip 11 may be connected to a next adjacent clip by a narrow rib or web in order to maintain the appropriate distance between the clips 11 after affixation.

The clips 11 may be held within the lumen 18 by a variety of methods. In one such method, the clips may be loosely coupled to the inner wall of body 12. For example, a biocompatible adhesive may be applied to a side of the clip 11 which contacts the inner wall of the body 12. The adhesive may be chosen such that a relatively small predetermined force is capable of decoupling the clips 11 from the body 12. Alternatively, the clips may be snap fit into the body 12. Alternatively, the clips 11 may be heat welded or ultrasonically welded to the inner wall of the body 12, depending on the material forming the clip and the body. Still further, the clips 11 may be formed integrally with the body 12, and may include a region that is readily fractured or broken to separate the clips 11 from the body 12. In each of these arrangements, the clips 11 may be readily detached from the body 12 by the application of a small pulling force, or by operation of an optional scraper (not shown) that may be slidably disposed within body 12. It will be understood that any suitable method of coupling the clips 11 to the inner wall of body 12 may be used so long as the attachment between the clips and body is severable as necessary.

FIGS. 3A-3C illustrate a method of using the device 10 for repairing the posterior valve 2 of the mitral valve. With the clips 11 loaded in body 12, device 10 may be inserted into a patient and advanced until the distal end 14 of body 12 is located adjacent the mitral valve leaflets, preferably using a transseptal approach. That is, the device 10 may be advanced from the femoral vein through the iliac vein, the interior vena cava, and the right atrium, and across the septum wall into the left atrium, until the distal end 14 of body 12 is positioned adjacent the posterior leaflet 2 and the anterior leaflet 3 of the mitral valve. This route requires the least amount of bending or turning and provides a relatively direct route to the mitral valve leaflets. Minimizing the number of turns may facilitate the operative control over device 10. Any other approach may be used to position body 12 adjacent the mitral valve leaflets, including, in particular, a transapical approach. If the distal end 14 of body 12 or adjacent structures are formed from or include echogenic materials, the distal end of the body may be guided to a position adjacent leaflets 2 and 3 using two-dimensional or three-dimensional echocardiography.

After device 10 has been positioned so that the distal end 14 thereof lies adjacent the mitral valve leaflets, a mechanism may be deployed from device 10 or otherwise operated to pull or draw the tissue of a selected leaflet, in this case posterior leaflet 2, into lumen 18 through the open distal end 14 of body 12. In one example, shown in FIGS. 3A-3C, device 10 may include a wire 32 that may be deployed, for example, from lumen 18. The wire 32 may be formed as a guidewire, and may include an angled rod or hook at its distal end for capturing and pulling the loose tissue. It will be understood that wire 32 may be fashioned in any desired configuration and in different arrangements for effectively pulling loose tissue into the lumen 18.

Wire 32 may be formed of a shape memory metal such as, for example, nitinol. In arrangements in which the wire 32 is disposed within the elongated body 12, the use of a shape memory metal allows the wire to have a first, linear configuration when fully retracted within body 12 and a second, hook-shaped configuration when the wire is deployed outside body 12, or outside a secondary body that may be inside body 12. At the outset of a procedure, the user may begin with a fully retracted wire 32. The wire 32 may then be deployed outside the elongated body 12 to capture tissue. As the wire 32 is deployed, it may begin to form a hook shape. The hook-shaped wire 32 may then be used to grab the posterior leaflet 2 and pull it proximally into the lumen 18 through the open distal end 14 of body 12.

As the leaflet 2 is pulled into the lumen 18, it forms a gathered configuration, which includes a bundled portion of loose leaflet tissue, resulting in a tightening in the remaining portions of the leaflet 2. As it is pulled further into lumen 18, the gathered leaflet tissue will be pulled through a first clip 11a which engages the leaflet. The clip 11a may be coupled to the interior of the body 12 and biased to become firmly affixed to the leaflet 2, such that the leaflet is unable to be unfastened once engaged by the clip. Once the distal-most clip 11a has engaged the leaflet 2, the effects on regurgitation may be assessed by measuring the volume or rate of flow through the heart valve. If regurgitation has been eliminated or adequately curtailed, the user may begin the process to remove device 10 from the patient, as will be described below. If, however, it is found that a second clip 11 would be desirable, the user may pull the tissue of the leaflet 2 further into the lumen 18 by pulling proximally on wire 32. A clip 11 may be coupled to the gathered leaflet 2 each time the leaflet 2 travels a predetermined distance within lumen 18. In at least some examples, this predetermined distance is the same distance between clips 11. For example, a clip 11 may be coupled to leaflet 2 each time leaflet 2 travels 1 mm.

As seen in FIG. 3B, the leaflet 2 has been pulled from a first position, shown in FIG. 3A with cross-hatching, to a second position, shown in FIG. 3B with downward-diagonal hatching, such that two clips 11a and 11b have now engaged the leaflet. Again, regurgitation is assessed and the effects of the second clip 11b are evaluated. If regurgitation has been adequately curtailed, the user may remove device 10 from the patient; if not, the leaflet tissue may be pulled further into lumen 18 until engaged by a third clip 11c, as shown in FIG. 3C. As illustrated in FIG. 3C, the leaflet 2 has been pulled to a third position, shown with horizontal hatching, and all three clips 11a, 11b and 11c are affixed to the leaflet.

As discussed earlier, the device 10 may include any number of clips 11 and additional clips may be employed if necessary. The leaflet 2 may be pulled into the lumen 18 and may be engaged by a series of clips 11 in a ratchet-like manner, allowing for a single direction of motion of the leaflet 2. That is, once the leaflet 2 is pulled through a clip 11, the clip engages the leaflet 2 and prevents the leaflet from traveling in the reverse direction toward the distal end 14 of the device 10. Instead, the leaflet 2 is either maintained in its position or pulled further into lumen 18. As described above, the shape and configuration of clips 11 may be helpful in providing this ratchet action to prevent the leaflet 2 from being released from the device 10 and to allow for sequential applications of clips 11 as necessary.

If, after affixing one or more clips 11, it is seen that the clips have adequately remedied regurgitation and/or leakage in the heart valve, the leaflet 2 with the affixed clips may be removed from the device 10. With clips 11 firmly affixed to the leaflet 2, removal of the leaflet from the device 10 may simply involve pulling the leaflet from the distal end of the device to separate the leaflet from the device. Pulling on the leaflet 2 may sever a portion of clips 11 at their fracture region, release the snap fit, or break the weld or adhesive that couples the clips 11 to the body 12 depending on the method of attachment. In at least some embodiments, a scraper 36 may be used to detach the clips 11 from the body 12. In one example, scraper 36 may be a thin-walled tube that is concentric to body 12. As seen in FIG. 3C, scraper 36 may be advanced toward the distal end of device 10 after all desired clips 11 have been secured to tissue. Any clips 11 that are not firmly affixed to the leaflet 2 may remain in the body 12 of the device 10 and will be removed from the patient as the device is removed.

Figure 4:
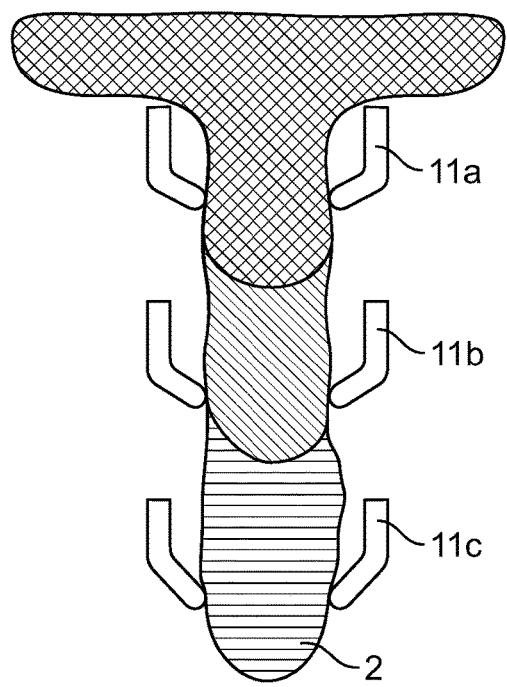
FIG. 4 is a highly schematic longitudinal cross-section showing a plurality of clips affixed to the gathered leaflet tissue of FIG. 3C after removal of the repair device.

FIG. 4 shows a posterior leaflet 2 that has been removed from the device 10, the clips 11a, 11b and 11c being fastened to the leaflet. The clips 11 maintain the leaflet tissue in its gathered configuration. As a result, the gathered configuration of the tissue may change the shape of the leaflet 2, tightening loose or floppy tissue therein. This tightening of the leaflet tissue may reduce the likelihood of prolapse and mitral valve regurgitation, thereby repairing the functionality of the valve. Clips 11 may be formed from or include an echogenic material to enable the clips, and their final deployed positions, to be visualized using three-dimensional echocardiography.

The device 10 may be actuated by an operating mechanism (not shown). In one example, the device 10 may include an electrically operated motor for controlling the movement of wire 32 in the proximal and distal directions. Wire 32 may be coupled to the motor such that, by depressing, sliding, or rotating an actuating member on a handle (not shown) of device 10, the motor may be operated to deploy/retract the wire.

Figure 5:
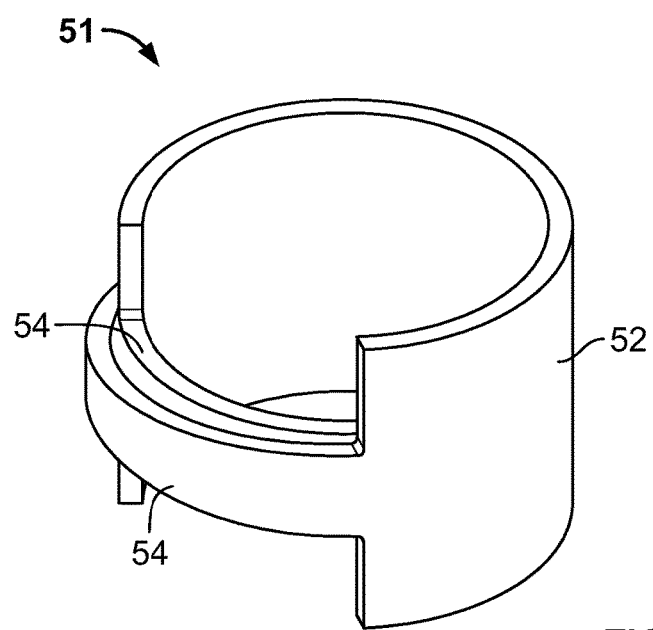
FIG. 5 is a perspective view of a second embodiment of a clip for use in the present invention.
Figure 6:
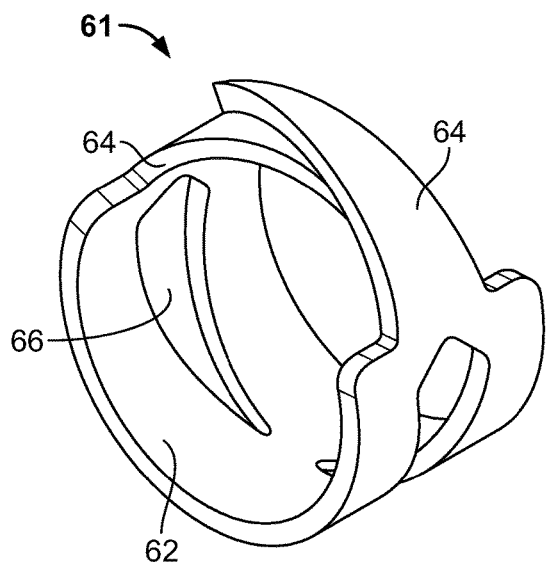
FIG. 6 is a perspective view of a third embodiment of a clip for use in the present invention.
Figure 7:
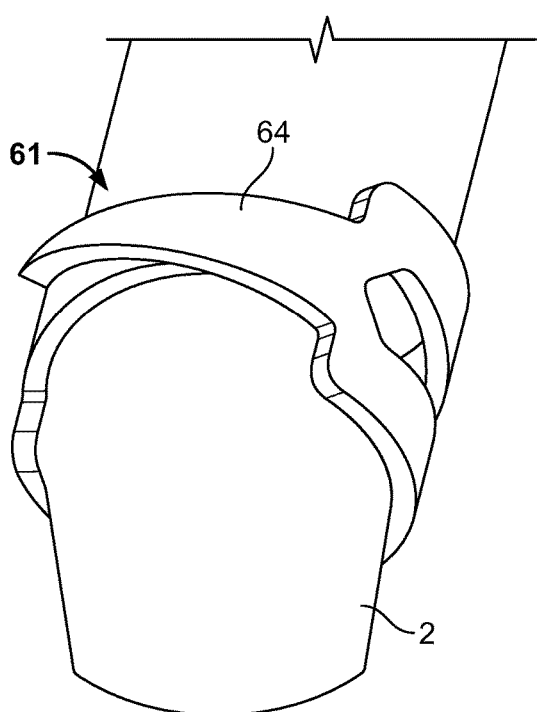
FIG. 7 is a perspective view of the clip of FIG. 6 as applied to leaflet tissue.

In an alternative embodiment, instead of a plurality of clips 11 arranged in series in the longitudinal direction of body 12, a plurality of clips, such as those seen in FIGS. 5-7, may be applied to the leaflet tissue at the same position within the body. This embodiment will be described in more detail with reference to FIGS. 8-10.

Figure 8A:
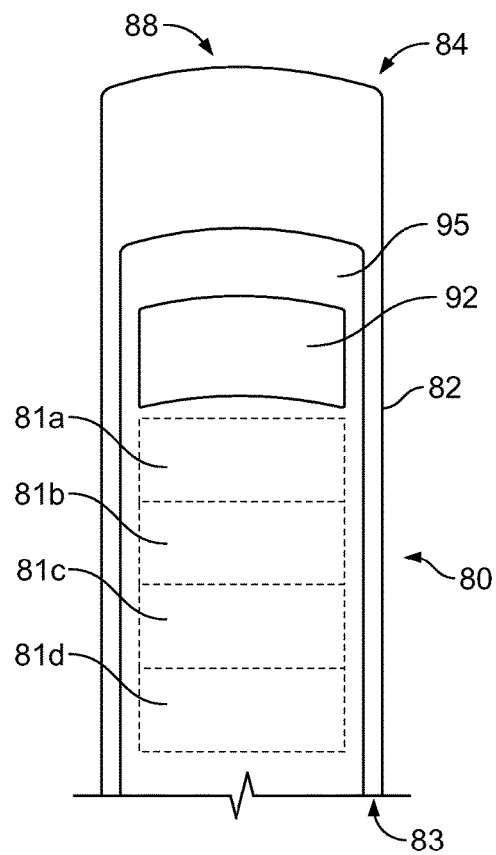
FIG. 8A is a schematic front view of a second embodiment of a device for repairing heart valve leaflets in accordance with the present invention.
Figure 8B:
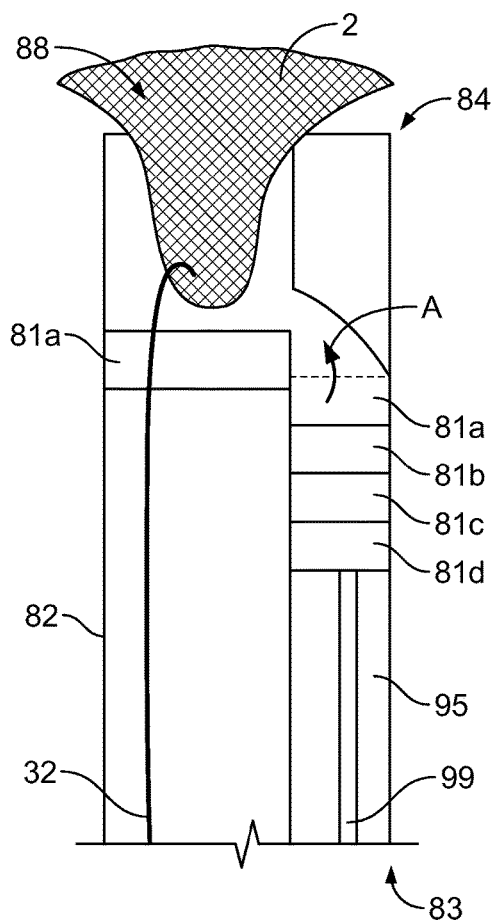
FIG. 8B is a schematic side view of the device of FIG. 8A with a valve leaflet extending into the distal end thereof.
Figure 9:
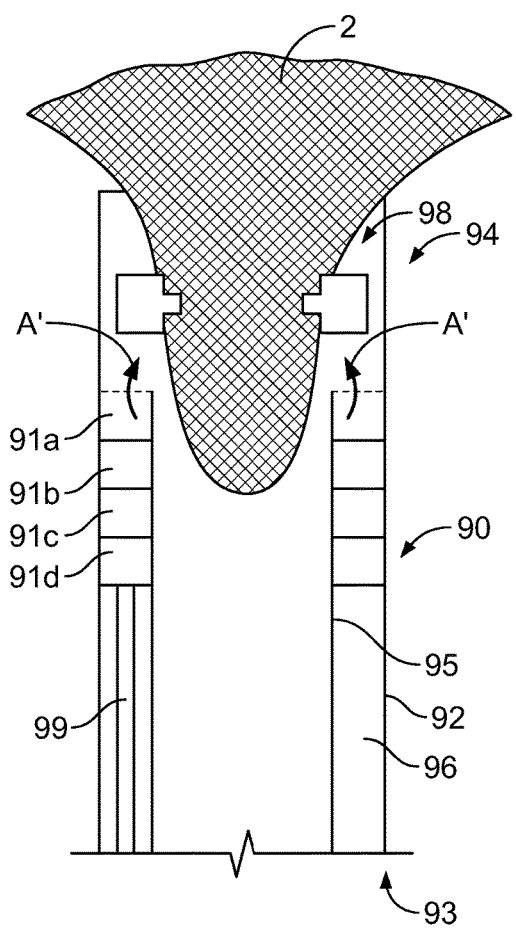
FIG. 9 is a schematic front view of a third embodiment of a device for repairing heart valve leaflets in accordance with the present invention.

FIGS. 5-7 show several examples of a clip that may be used in the embodiment of FIGS. 8-10. Referring to FIG. 5, a clip 51 may include a substantially cylindrical frame 52. Each side of the frame 52 may terminate in an arm 54, with the two overlapping arms 54 completing the substantially cylindrical configuration of the frame. Each arm 54 may taper in width or otherwise be formed with a prong on its free end. These prongs may become embedded in the leaflet tissue when clip 51 is deployed. The clip 51 may be mounted in the lumen of body 12 through the use of a weld, an adhesive, a fracture region or other mechanism as described above in connection with clips 11. When mounted in lumen 18, clip 51 may be held in an expanded configuration, with arms 54 not overlapping, or overlapping to a lesser extent than shown in FIG. 5. The clip 51 may be made of a memory metal, such as nitinol, and may be biased to curl into the substantially cylindrical contracted configuration of FIG. 5 once the clip is detached from body 12.

FIG. 6 shows a clip 61 having a slightly different structure than clip 51. Clip 61 includes a substantially cylindrical frame 62 with an overlapping arm 64 on each side of the frame. Each arm 64 may be shaped as a prong which may become embedded in the leaflet tissue when clip 61 is deployed. Clip 61 also includes a pair of cutouts 66 in the frame 62. Cutouts 66 serve to relieve stress on frame 62. The clip 61 may be mounted in the lumen 18 of body 12 in the same expanded configuration, and using the same mechanisms, as clip 51. As seen in FIG. 7, when the leaflet 2 or other tissue is positioned within the clip 61, the clip may break off or otherwise become disengaged from the body 12, returning to its contracted configuration and becoming affixed to the leaflet. FIG. 7 shows the clip constraining and thereby securing itself to the tissue circumferentially. Alternatively, the clip may be secured to the tissue by having its prongs embedded in the tissue.

FIG. 8A shows a schematic front view of a device 80 having a clip elevator mechanism for advancing clips, such as those described in FIGS. 5 and 6, to a deployment position. The device 80 is similar to the device 10 of FIGS. 2-3 and includes an elongated tubular body 82 having a proximal end 83, a distal end 84 and a lumen 88 extending from the proximal end to the distal end, the distal end being open.

The device 80 further includes a deployment tube 95 arranged within the body 82. The deployment tube 95 may be configured as a cylindrical sheath for housing the clips 81. FIG. 8B is a schematic side view of the device 80 of FIG. 8A and illustrates how the deployment tube 95 is arranged within and to one side of the body 82. A plurality of clips 81a, 81b, 81c and 81d are axially disposed within deployment tube 95. Although the figures illustrate four clips, device 80 may include more or less than four clips as desired. Clips 81 may have the structure of clips 51 or 61 described above. The clips 81 may be compressed within deployment tube 95 in order to reduce the overall diameter of device 80.

The deployment tube 95 may include a slot 92 that allows communication between the interior of the deployment tube and lumen 88. Slot 92 may be configured as a window, hole or aperture that allows the clips 81 to be advanced from the deployment tube 95 to the lumen 88. Deployment tube 95 may further house a feeder mechanism 99 that advances the clips 81 distally through the deployment tube toward slot 92. Feeder mechanism 99 may include a pushrod or the like that may be biased by a compression spring to advance the clips 81 distally, or that is coupled to an electric motor that may be actuated as needed to advance the clips toward slot 92.

Feeder mechanism 99 advances the clips 81 toward the slot 92 in order to introduce the clips 81 into lumen 88. The deployment tube 95 may be curved at its distal end or device 80 may include a curved or inclined deflecting member at the distal end of deployment tube 95 so that the axial force exerted by the feeder mechanism 99 not only advances the clips 81 in a longitudinal direction as indicated by the arrow A, but also pushes the clips 81 out of deployment tube 95 and into lumen 88 for engaging leaflet 2. FIG. 8B shows a clip 81a which has been advanced from a position within the deployment tube 95 (shown in phantom lines) to a position within lumen 88 for engaging the leaflet 2. Clip 81a, as well as subsequent clips 81, may be biased to expand from their previously compressed condition in deployment tube 95 to an expanded condition within lumen 88. This expanded condition may be the relaxed condition of clips 81 (e.g., the shape that is assumed when no external forces are applied), or may be a slightly compressed condition, but less than the degree of compression deployment tube 95. The radial force exerted by a slightly compressed clip 81 will help hold the clip in place in lumen 88. With clip 81a in lumen 88, the leaflet 2 may be pulled further into the lumen using wire 32. Leaflet 2 may then be pulled through the expanded clip so that the clip becomes affixed to the leaflet and grasps the leaflet in the gathered configuration. As leaflet 2 is pulled toward the proximal end 83 of the device using wire 32, clip 81a is coupled to the leaflet and pulled toward the proximal end 83 of the device as well. The effects on regurgitation may be assessed at this time and if regurgitation has not been eliminated or adequately curtailed, feeder mechanism 99 may then be used to advance clip 81b as indicated by the arrow A out of deployment tube 95 and into lumen 88 to engage leaflet 2 at a position distal to clip 81a. This process of advancing additional clips may be repeated until regurgitation has been eliminated or adequately curtailed, or when the maximum number of clips in the device 80 have been engaged into leaflet 2. Even if clips 81 expand slightly, once removed from lumen 88, the amount of expansion will be small, and the clips will still remain affixed to the gathered leaflet tissue.

Although several methods of advancing clips 81 within device 80 using a feeder mechanism 99 have been described above, it will be understood that additional configurations and arrangements of deployment tube 95 within device 80 and different methods of advancing clips 81 within device 80 may be utilized, and that the present disclosure is not limited to such configurations.

FIG. 9 illustrates a device 90 having an alternative clip elevator mechanism. The device 90 includes a tubular body 92 having a proximal end 93, a distal end 94 and a lumen 98 extending from the proximal end to the distal end, the distal end being open. The device 90 further includes a deployment tube 95 disposed within body 92 concentrically with lumen 98. In effect, deployment tube 95 divides lumen 98 into two portions, a first portion which is the lumen within deployment tube 95, and second portion which is the annular space 96 between the deployment tube and the tubular wall of body 92. A plurality of clips 91a, 91b, 91c, and 91d are disposed within annular space 96 so that the arms thereof are wrapped around deployment tube 95. Clips 91 may have the structure of clips 51 or 61 described above. The clips 91 may be made of nitinol or another shape-memory material and may be disposed around deployment tube 95 so that they are expanded beyond their relaxed shape. The clips 91 may be pushed toward the distal end of body 92 as indicated by arrows A' using a feeder mechanism 99 that may be similar to the feeder mechanisms described above in connection with device 80. As they are pushed distally, the clips 91 will travel in the expanded condition along the exterior of deployment tube 95. As the clips 91 reach the distal end of deployment tube 95, they eventually will be pushed off of same. No longer being constrained by the deployment tube 95, the clips 91 will contract to their natural configuration around the leaflet 2. As seen in FIG. 9, clip 91a has been advanced from an initial position (shown in phantom lines) within the annular space 96 to an engagement position within the lumen 98 to secure leaflet 2. Additional clips 91b, 91c and 91d may be advanced toward the distal end of the deployment tube 95 using the feeder mechanism 99 as needed. Although the foregoing describes the use of four clips 91, it will be appreciated that device 90 may include more or less than four clips as desired.

To use the device 90 for repairing heart valve leaflet tissue, the elongated body 92 may be inserted into the patient and advanced to the mitral valve, preferably using a transseptal approach in a manner similar to device 10 above. If the distal end 94 of body 92 or adjacent structures include echogenic materials, the distal end of the body may be guided to a position against a leaflet at the coaption line 5 using two-dimensional or three-dimensional echocardiography.

Once device 90 has reached the leaflet 2, a wire or another mechanism may be deployed to grasp or capture a loose portion of leaflet 2 and pull it within lumen 98. On deployment, the shape of the wire may change from a linear configuration within the body 92 to a hook-shaped configuration capable of grasping and pulling loose tissue. When the leaflet 2 is pulled into the lumen 98, the loose tissue forms into a gathered configuration, resulting in a tightening in the remaining portions of the leaflet. At this juncture, one or more clips 91 may be applied to the tissue to hold it in the gathered configuration.

Figure 10C:
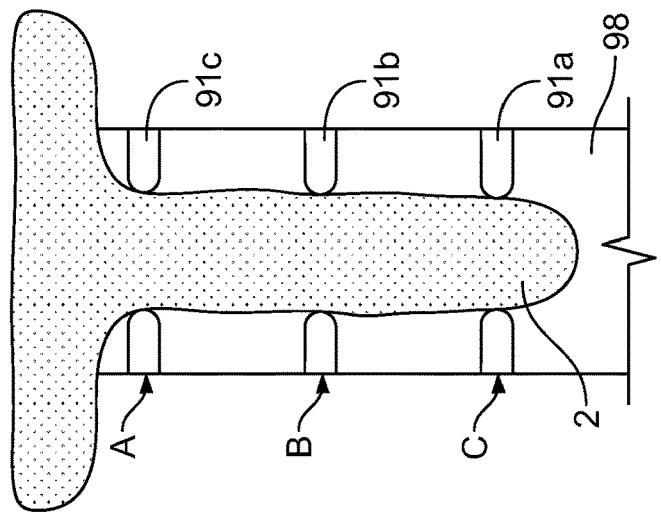
FIGS. 10A-10C are illustrative views showing the advancement and translation of the clips using the device of FIG. 9.
Figure 10B:
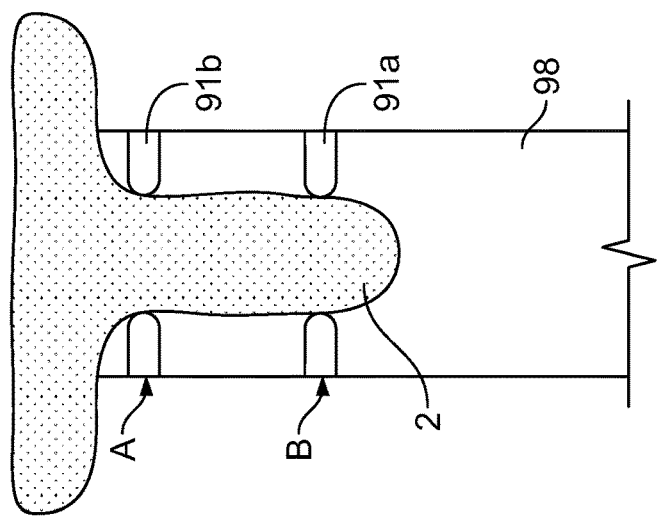
Figure 10A:
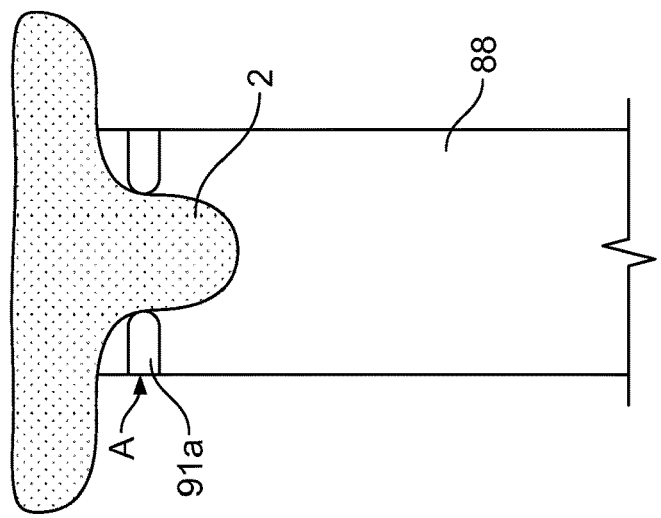
Figure 11:
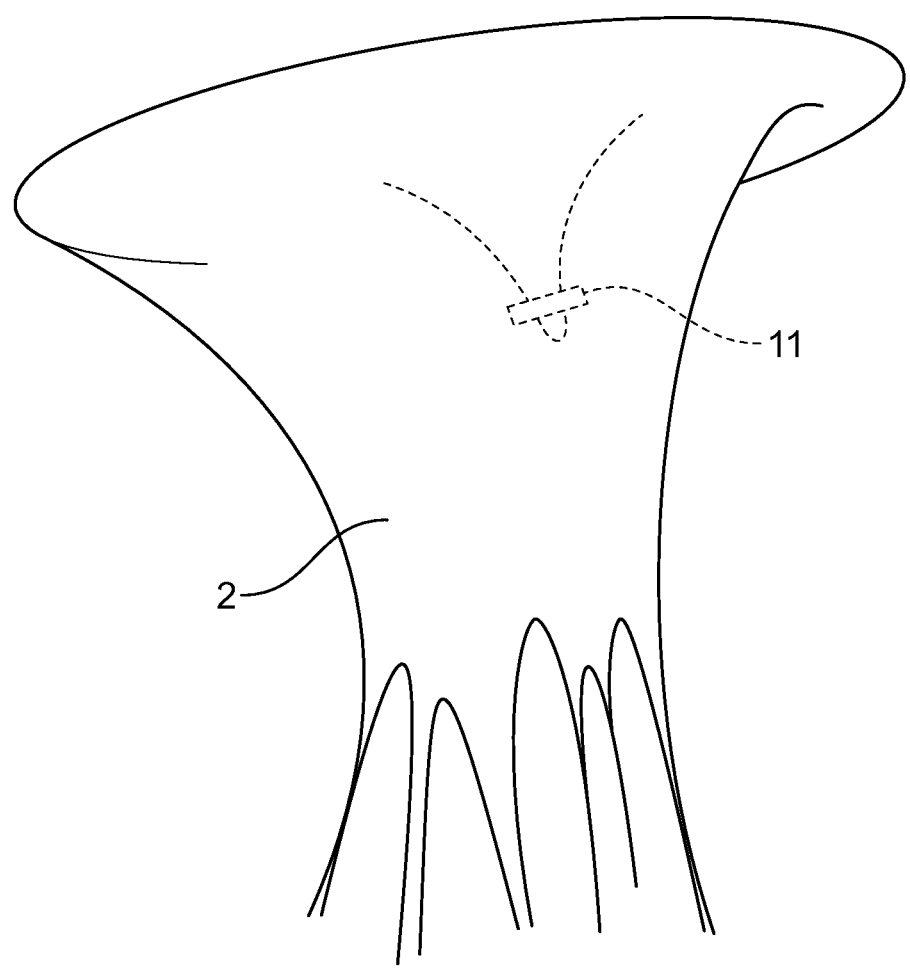
FIG. 11 is an illustrative view of a repaired mitral valve leaflet.

FIGS. 10A-10C are schematic illustrations showing the application of clips 91 to the loose tissue of leaflet 2. For clarity, the deployment tube 95 is not shown in these figures. As seen in FIG. 10A, a first clip 91a is advanced to position A for engaging leaflet 2. After clip 91a has been securely affixed to the gathered configuration of leaflet 2, the effects of clip 91a on valve function (e.g., regurgitation and leakage) may be assessed. If additional clips 91b, 91c, 91d, etc. are necessary, the tissue bearing clip 91a may be pulled toward the proximal end 93 of device 90 until clip 91a is at or near position B, proximal of position A. The pulling of the tissue may be accomplished via wire 32 which, for purposes of clarity, is also not shown in the figure. With clip 91a now at position B, position A is free to receive an additional clip 91b. Feeder mechanism 99 may advance clip 91b to position A where it will engage leaflet 2. The effects of clips 91a and 91b on valve function may again be measured. If valve functioning is still inadequate, the tissue bearing clips 91a and 91b may be pulled further inwardly until the clips are at or near positions C and B, respectively, freeing up position A for accepting clip 91c. This process of engagement, assessment and advancement may be repeated any number of times until the desired number of clips 91 have been affixed to leaflet 2 and the functioning of the valve is acceptable. The device 90 may then be removed from the body, leaving behind the leaflet 2 in the gathered configuration with the clips 91 secured thereto.

In at least some variations, the wire 32 and the feeder mechanism 99 may both be coupled to a motor for translation within the device lumen. Thus, once wire 32 grasps a portion of leaflet 2, the leaflet 2 may be pulled through lumen 98 and the clips 91 may be advanced for deployment by actuating the motor, such as by operation of a button. In practice, a single button may be pressed to both advance the clips 91 with the feeder mechanism 99 and to pull the wire 32 coupled to leaflet 2. By pressing and holding the button, multiple clips 91 may be advanced and deployed until enough clips 91 have been affixed to the leaflet 2.

In any of the embodiments described, the distal end of the device, into which the posterior leaflet 2 enters, may be placed adjacent to the upper portion 6 of the proximal leaflet 2, the lower portion 7 of the proximal leaflet 2, or on the underside (opposite side) of the proximal leaflet.

In the devices shown in the figures, particular structures are shown that are adapted to grasp, secure, and repair heart valve leaflet tissue. The invention also contemplates the use of any alternative structures for such purposes, including structures having different lengths, shapes, and configurations.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A device for repair of a heart valve leaflet, the device comprising:
    an elongated body having a lumen extending therethrough in a longitudinal direction, a proximal end, and an open distal end; and
    a plurality of clips disposed at spaced positions within the lumen, each of the plurality of clips having a first opening with a first diameter at a first end thereof and a second opening with a second diameter at a second end thereof, each of the clips having a first configuration for receiving the leaflet and a second configuration for repairing the leaflet, in the first configuration, the first opening facing the open distal end of the elongated body, the second opening facing the proximal end of the elongated body, and the first diameter being greater than the second diameter, and in the second configuration, the first opening facing the open distal end of the elongated body, the second opening facing the proximal end of the elongated body, and the first diameter being greater than the second diameter, the plurality of clips being configured and arranged to couple to a portion of the heart valve leaflet,
    wherein at least one clip in the plurality of clips and the heart valve leaflet are capable of translation relative to one another in the longitudinal direction.

2. The device of claim 1, wherein the plurality of clips are bowl shaped and the portion of the heart valve leaflet is able to move in one direction relative to the clips but is inhibited from moving in a second direction opposite the one direction.

3. The device of claim 1, wherein the plurality of clips includes three clips.

4. The device of claim 1, further comprising a frangible weld to couple the plurality of clips to the elongated body.

5. The device of claim 1, wherein the plurality of clips are affixed to the elongated body at the spaced positions.

6. The device of claim 1, further comprising a wire slidably disposed within the lumen and configured and arranged to pull the portion of the heart valve leaflet into the lumen through the open distal end.

7. The device of claim 6, wherein the wire is slidably disposed in the lumen for movement between a retracted position and a deployed position, the wire being formed of a memory metal, a distal portion of the wire having a linear configuration when the wire is in the retracted position and a hook-shape configuration when the wire is in the deployed position.

8. The device of claim 1, further comprising:
    a feeder mechanism interposed between the plurality of clips and the proximal end of the elongated body; and
    actuating device for actuating the feeder mechanism to move at least one of the plurality of clips toward the open distal end of the elongated body.

9. The device of claim 8, wherein each of the plurality of clips is independently moveable toward the open distal end of the elongated body.

10. The device of claim 1, wherein each of the clips is adapted to flex radially outward upon receipt of the leaflet.

* * * * *